(12) United States Patent
Lazaro et al.

(10) Patent No.: US 7,507,766 B2
(45) Date of Patent: Mar. 24, 2009

(54) TREATMENT OF CANCERS

(75) Inventors: Luis Lopez Lazaro, Madrid (ES); Jose Maria Fernandez-Sousa, Madrid (ES); Jean-Pierre Armand, Villejuif-Cedex (FR); Eric Raymond, Villejuif-Cedex (FR)

(73) Assignee: Pharma Mar, S.A., Madrid (ES)

(*) Notice: Subject to any disclaimer, the term of this patent is extended or adjusted under 35 U.S.C. 154(b) by 345 days.

(21) Appl. No.: 10/398,835

(22) PCT Filed: Oct. 12, 2001

(86) PCT No.: PCT/GB01/04555

§ 371 (c)(1),
(2), (4) Date: Aug. 1, 2003

(87) PCT Pub. No.: WO02/30441

PCT Pub. Date: Apr. 18, 2002

(65) Prior Publication Data

US 2004/0010043 A1      Jan. 15, 2004

(30) Foreign Application Priority Data

| Oct. 12, 2000 | (GB) | ............................. 0025044.9 |
| Oct. 13, 2000 | (GB) | ............................. 0025209.8 |
| Nov. 15, 2000 | (WO) | ................... PCT/GB00/04349 |
| Mar. 23, 2001 | (GB) | ............................. 0107373.3 |

(51) Int. Cl.
*A61K 31/195* (2006.01)

(52) U.S. Cl. .................................... 514/565; 435/6

(58) Field of Classification Search .............. None
See application file for complete search history.

(56) References Cited

U.S. PATENT DOCUMENTS

| 4,493,796 | A | 1/1985 | Rinehart, Jr. |
| 4,670,262 | A | 6/1987 | Battelli et al. |
| 5,294,603 | A | 3/1994 | Rinehart |
| 5,462,726 | A | 10/1995 | Lodge |
| 5,834,586 | A | 11/1998 | Rinehart et al. |
| 5,883,135 | A | 3/1999 | Gyory et al. |
| 6,030,943 | A | 2/2000 | Crumb et al. |
| 6,034,058 | A | 3/2000 | Rinehart et al. |
| 6,080,877 | A | 6/2000 | Swindell et al. |
| 6,153,731 | A | 11/2000 | Rinehart et al. |
| 6,156,724 | A | 12/2000 | Rinehart et al. |
| 6,509,315 | B1 | 1/2003 | Joullié et al. |
| 6,610,699 | B2 | 8/2003 | Cavazza et al. |
| 6,710,029 | B1 | 3/2004 | Rinehart et al. |
| 6,890,904 | B1 | 5/2005 | Wallner et al. |
| 7,064,105 | B2 | 6/2006 | Joullié et al. |
| 2001/0021380 | A1 | 9/2001 | Pluenneke |
| 2002/0098185 | A1 | 7/2002 | Sims et al. |
| 2003/0044893 | A1 | 3/2003 | Baum et al. |

FOREIGN PATENT DOCUMENTS

| EP | 0 048 149 A1 | 3/1982 |
| EP | 0 393 883 | 10/1990 |
| ES | 2 102 322 | 7/1997 |
| WO | WO 91/04985 | 4/1991 |
| WO | WO 93/00362 | 1/1993 |
| WO | WO 98/01352 | 1/1998 |
| WO | WO 98/17275 | 4/1998 |
| WO | WO 98/17302 | 4/1998 |
| WO | WO 99/42125 | 8/1999 |
| WO | WO 00/06134 | * 2/2000 |
| WO | WO 00/71135 | 11/2000 |
| WO | WO 01/35974 | 5/2001 |
| WO | WO 01/76616 | 10/2001 |
| WO | WO 02/02596 | 1/2002 |
| WO | WO 02/30441 | 4/2002 |
| WO | WO 03/033013 | 4/2003 |
| WO | WO 2004/080421 A2 | 9/2004 |

OTHER PUBLICATIONS

Faircloth et al. "Aplidine (APL) is a novel marine derived depsipeptide with in vivo antitumor activity" 1998, Proceedings of the American Association for Cancer Research, vol. 39, pp. 227.*

Ady-Vago "L-carnitine as a protector against aplidine induced skeletal muscle toxicity" Proceeding of the American Association of Cancer Research Annual meeting (Mar. 2001) vol. 42, pp. 545.*

Faircloth, Annals of Oncology, 1998, 9 (suppl. 2) 33.*

Ady-Vago, Proceeding of the American Association of cancer research annual meeting, 2001, vol. 42, pp. 545.*

Faircloth, Annals of oncology, 1998, 9 (suppl. 2) 33.*

Ady-Vago, N. et al., "L-Carnitine as a Protector Against Aplidine Induced Skeletal Muscle Toxicity", *Proceedings of the American Association for Cancer Research*, vol. 42, pp. 545 (Mar. 2001).

Bergeron, Raymond J. et al., "Antineoplastic and Antiherpetic Activity of Spermidine Catecholamide Iron Chelators", *Biochemical and Biophysical Research Communications*, vol. 121, No. 3, pp. 848-854 (1984).

Broggini, M. et al., "Aplidine Blocks VEGF Secretion and VEGF/VEGF-RI Autocrine Loop in a Human Leukemic Cell Line", *11th NCI-EORTC-AACR on New Drugs in Cancer Therapy*, Amsterdam (2000), Abstract 21.

Chapa, A.M. et al., "Influence of Intravenous L-Carnitine Administration in Sheep Preceding an Oral Urea Drench$^{1,2}$", *Journal of Animal Science*, vol. 76, No. 11, pp. 2930-2937 (1998).

Depenbrock, H. et al., "In vitro activity of aplidine, a new marine-derived anti-cancer compound, on freshly explanted clonogenic human tumour cells and haematopoietic precursor cells", *British Journal of Cancer*, vol. 78, No. 6, pp. 739-744 (1998).

Erba, E. et al., "Cell cycle phases perturbations induced by new natural marine compounds", *Annals of Oncology*, vol. 7, Supplement 1, #283, pp. 82 (1996).

Faircloth, G. et al., "Aplidine (APL) is a novel marine-derived depsipeptide with in vivo antitumor activity", *Proceedings of the American Association for Cancer Research*, vol. 39, #1551, pp. 227 (1998).

(Continued)

*Primary Examiner*—Christopher R. Tate
*Assistant Examiner*—Roy Teller
(74) *Attorney, Agent, or Firm*—Fish & Richardson P.C.

(57) ABSTRACT

Carnitine and other muscle protectors are useful to prevent side effects of aplidine and aplidine analogues.

9 Claims, 3 Drawing Sheets

OTHER PUBLICATIONS

Faircloth, G. et al., "Dehydrodidemnin B (DDB) a new marine derived anti-cancer agent (MDA) with activity against experimental tumor models" and "Biological activity of thiocoraline. A new depsipeptide from a marine micromonospora", *Annals of Oncology*, vol. 7, Supplement 1, #111 and #112, pp. 34 (1996).

Faircloth, G. et al., "Preclinical characterization of Aplidine (APD), a new marine anticancer depsipeptice (MADEP)", *Proceedings of the American Association for Cancer Research*, vol. 38, #692, pp. 103 (1997).

Faircloth, G. et al., "Preclinical development of aplidine, a novel marine-derived agent with potent antitumor activity", *Annals of Oncology*, vol. 9, Supplement 2, #129, pp. 34 (1998).

Faircloth, G. et al., "Schedule-dependency of aplidine, a marine depsipeptide with antitumor activity", *Proceedings of the American Association for Cancer Research*, vol. 40, #2612, pp. 394-395 (1999).

Geldof, Albert A. et al., "Cytotoxicity and neurocytotoxicity of new marine anticancer agents evaluated using in vitro assays", *Cancer Chemother. Pharmacol.*, vol. 44, pp. 312-318 (1999).

Genin, Michael J. et al., "Synthesis and Crystal Structure of a Peptidomimetic Containing the (R)-4,4-Spiro Lactam Type-II β-Turn Mimic", *Journal of Organic Chemistry*, vol. 58, No. 8, pp. 2334-2337 (1993).

Gomez-Fabre, P.M. et al., "Polamine contents of human breast cancer cells treated with the cytotoxic agents chlorpheniramine and dehydrodidemnin B", *Cancer Letters*, vol. 113, Nos. 1, 2, pp. 141-144 (1997).

Jimeno et al., "A Correlation of Selective Antitumor Activities of the Marine-Derived Compound Aplidine Using Different Models", *10th NCI-EORTC-AACR Symposium on Molecular Targets and Cancer Therapeutics*, Washington (1999), Abstract 311.

Jou, Gemma et al., "Total Synthesis of Dehydrodidemnin B. Use of Uronium and Phosphonium Salt Coupling Reagents in Peptide Synthesis in Solution", *Journal of Organic Chemistry*, vol. 62, No. 2, pp. 354-366 (1997).

Lobo, C. et al., "Effect of Dehydrodidemnin B on Human Colon Carcinoma Cell Lines", *Anticancer Research*, vol. 17, No. 1A, pp. 333-336 (1997).

Chauhan, D. et al., "Multiple Myeloma Cell Adhesion-Induced Interleukin-6 Expression in Bone Marrow Stromal Cells Involves Activation of NF-κB," *Blood*, 87(3):1104-1112 (1996).

"Didemnin B," *Drugs of the Future*, 20(1):77 (1995).

Faircloth, G. et al., "Marine (MA) Depsipeptides (DEP) with Activity (A) against Solid Tumours (ST) Models," *Proceedings 8th ECCO Congress*, 31A (Suppl. 5):S29, Abstract No. 122 (1995).

Faircloth, G. et al., "Preclinical Development of Aplidine, a Novel Marine-Derived Agent with Potent Antitumor Activity," *Annals of Oncology*, 9 (Suppl. 2):34, Abstract No. 129 (1998).

Giovanella, B.C. et al., "Correlation Between Response to Chemotherapy of Human Tumors in Patients and in Nude Mice," *Cancer*, 52(7):1146-1152 (1983).

Hideshima, T. et al., "The Proteasome Inhibitor PS-341Inhibits Growth, Induces Apoptosis, and Overcomes Drug Resistance in Human Multiple Myeloma Cells," *Cancer Res.*, 61:3071-3076 (2001).

Hudes, G.R., "Phase II trial of 96-hour paclitaxel plus oral estramustine phosphate in metastatic hormone-refractory prostate cancer", *J. Clin Oncol.*, 15(9):3156-63 (1997).

Jimeno, J. et al., "Translational Studies Supporting the Clinical Development of Aplidine (APL) in Pediatric Leukemia," *Annals of Oncology*, 13 (Suppl. 5):19, Abstract No. 65P (2002).

Matsuoka, M., "Comparison of the effects of l-carnitine, d-carnitine and acetyl-l-carnitine on the neurotoxicity of ammonia", *Biochemical Pharmacology*, (46(1):159-164 (1993).

Mayer, S.C. et al., "Synthesis of New Didemnin B Analogs for Investigations of Structure/Biological Activity Relationships," *J. Org. Chem.*, 59(18):5192-5205 (1994).

Mead Johnson Oncology Products, Taxol (Paclitaxel) Injection Labeling Revision (Apr. 9, 1998).

Mitsiades, C.S. et al., "TRAIL/Apo2L Ligand Selectively Induces Apoptosis and Overcomes Drug Resistance in Multiple Myeloma: Therapeutic Applications," *Blood*, 98(3):795-804 (2001).

Mitsiades, C.S. et al., "Activation of NF-kappaB and Upregulation of Intracellular Anti-Apoptotic Proteins via the IGF-1/Akt Signaling in Human Multiple Myeloma Cells: Therapeutic Implications," *Oncogene*, 21(37):5673-5683 (2002).

Mitsiades, N. et al., "Molecular Sequelae of Proteasome Inhibition in Human Multiple Myeloma Cells," *Proc Natl Acad Sci USA*, 99(22):14374-14379 (2002).

Mitsiades, N. et al., "The Proteasome Inhibitor PS-341 Potentiates Sensitivity of Multiple Myeloma Cells to Conventional Chemotherapeutic Agents: Therapeutic Applications," *Blood*, 101(6):2377-2380 (2003).

Mitsiades, N. et al., "Molecular Sequelae of Histone Deacetylase Inhibition in Human Malignant B Cells," *Blood*, 101(10):4055-4062 (2003).

Palangie, T. et al., "Dose-Intense Salvage Therapy After Neoadjuvant Chemotherapy: Feasibility and Preliminary Results," *Cancer Chemother. Pharmacol.*, 44 (Suppl.):S24-S25 (1999).

Rinehart, K., "Antitumor compounds from tunicates", Medicinal Research Reviews, 20(1):1-27; Wiley Interactive Science Journal, Pub. online Dec. 22, 1999.

Uchiyama, H. et al., "Adhesion of Human Myeloma-Derived Cell Lines to Bone Marrow Stromal Cells Stimulates Interleukin-6 Secretion," *Blood*, 82(12):3712-3720 (1993).

Virmani, M.A., "Protective actions of l-carnitine and acetyl-l-carnitine on the neurotoxicity evoked by mitochondrial uncoupling or inhibitors", Pharmacological Research, 32(6):383-389 (1995).

Weiss, R. et al., "A Phase II Trial of Didemnin B in Myeloma," *Investigational New Drugs*, 12(1):41-43 (1994).

Cecil Textbook of Medicine (Bennett, J.C. and Plum, F., eds.) 20th Edition, vol. 1, pp. 1004-1010 (1996).

Draetta et al., "Section V. Topics in Biology—Cell Cycle Control and Cancer", *Annual Reports in Medicinal Chemistry*, Chapter 25, pp. 241-248, 1996.

Geldof et al., "Cytotoxicity and Neurocytotoxicity of New Marine Anticancer Agents Evaluated Using in Vitro Assays", *Cancer Chemother. Pharmacol.*; 44 321-318, (1999).

Hansen et al., "Continuous 5-Fluorouracil (5FU) Infusion in Carcinoma of the Pancreas: A Phase II Study", *Am. J. Med. Sci.*, 295:91-93, (1988).

Robert S. Kerbel, "What is the Optimal Rodent Model for Anti-Tumor Drug Testing?", *Cancer and Metastasis Reviews*, 17: 301-304, (1999).

"Note for Guidance on Evaluation of Anticancer Medicinal Products in Man", *The European Agency for the Evaluation of Medicinal Products*, EMEA, London, England, CPMP/EWP/205/95 rev. 1 corr, 14 pages, (2001).

Raymond et al., 25th Congress of the European Society of Medicinal Oncology, Hamburg, Germany, Oct. 13-17, 2000, reported in the *Annals of Oncology*, vol. 11, Suppl. 4, Abstract 610PD, (2000).

Urdiales et al., "Antiproliferative Effect of Dehydrodidemnin B (DDB), a Depsipeptide Isolated from Mediterranean Tunicates", *Cancer Letters*, 102:31-37, (1996).

Van-Boxtel et al., "*Drug Benefits and Risks: International Textbook of Clinical Pharmacology*", Chapter 9, pp. 91-102, (2001).

U.S. National Cancer Institute, U.S. National Institutes of Health, www.cancer.gov, "Cancer Topics—Colon and Rectal Cancer", http://www.cancer.gov/cancertopics/types/colon-rectal, 2 pages.

U.S. National Cancer Institute, U.S. National Institutes of Health, www.cancer.gov., "Gastric Cancer (PDQ®): Treatment—General Information About Gastric Cancer", http://www.cancer.gov/cancertopics/pdq/treatment/gastric/patient, 4 pages.

Mitsiades et al., "Pre-clinical studies in support of the clinical developments of Aplidin® (APL) for the treatment of multiple myeloma (MM)", Blood, Nov. 16, 2003, vol. 102, No. 11, p. 74a, abstract #250.

O'Neil, Maryadele J., Ann Smith and Patricia E. Heckelman, eds. The Merck Index—An Encyclopedia of Chemicals, Drugs, and Biologicals, Merck & Co., Inc., 13th Ed., p. 1791, (2001).

Luber-Narod, J. et al., "In Vitro Safety Profile of Aplidine, A Marine Natural Product with Chemotherapeutic Potential", *Proceedings of the AACR*, vol. 42, Abstract 374, Mar. 2001.

Mastbergen, S.C. et al., "Cytotoxicity and neurocytotoxicity of aplidine, a new marine anticancer agent evaluated using in vitro assays", *Annals of Oncology*, vol. 9, Supplement 2, #131 (1998).

Montgomery, D.W. et al., "Didemnin B Alters the Specific Binding of Prolactin to Human Lymphocytes and Decreases the Circulating Level of Prolactin in Mice", *Federal Proceedings*, vol. 44, No. 3, pp. 634, #1311 (1985).

Montgomery, David W. et al., "Didemnin B: A New Immunosuppressive Cyclic Peptide with Potent Activity In Vitro and In Vivo[b]", *Transplantation*, vol. 40, No. 1, pp. 49-56 (1985).

Nuijen, B. et al., "Pharmaceutical development of anticancer agents derived from marine sources", *Anti-Cancer Drugs*, vol. 11, pp. 793-811 (2000).

Raymond, Eric et al., "Preliminary Results of a Phase I and Pharmacokinetic Study of Aplidine Given as a 24-hour Infusion Every 2 Weeks in Patients With Solid Tumors and Non Hodgkin's Lymphomas", Proceedings of the American Association for Cancer Research, vol. 41, #3886 (2000).

Rinehart, K., "Didemnin and its Biological Properties", *Escom.*, pp. 626-631 (1987).

Rinehart, Kenneth L. et al., "Biologically Active Peptides and Their Mass Spectra", *Pure and Applied Chemistry*, vol. 54, No. 12, pp. 2409-2424 (1982).

Rinehart, Kenneth L. et al., "Didemnins and Tunichlorin: Novel Natural Products from the Marine Tunicate Trididemnum Solidum[b]", *Journal of Natural Products*, vol. 51, No. 1, pp. 1-21 (1988).

Rinehart, Kenneth L. et al., "Total Synthesis of Didemnins A, B and C[1,2]", *Journal of the American Chemical Society*, vol. 109, No. 22, pp. 6846-6848 (1987).

Rinehart, Kenneth L., Jr. et al., "Antiviral and antitumor compounds from tunicates[1,2]" *Federation Proceedings*, vol. 42, No. 1, pp. 87-90 (1983).

Rinehart, Kenneth L., Jr. et al., "Didemnins: Antiviral and Antitumor Depsipeptides from a Caribbean Tunicate", *Science*, vol. 212, No. 4497, pp. 933-935 (1981).

Rinehart, Kenneth L., Jr. et al., "Structure of the Didemnins, Antiviral and Cytotoxic Depsipeptides from a Caribbean Tunicate[b]", *Journal of the American Chemistry Society*, vol. 103, No. 7, pp. 1857-1859 (1981).

Sakai, Ryuichi et al., "Structure—Activity Relationships of the Didemnins [1,2]", *Journal of Medicinal Chemistry*, vol. 39, No. 14, pp. 2819-2834 (1996).

Seebach, Dieter et al., "Alkylation of Amino Acids without Loss of the Optical Activity: Preparation of α-Substituted Proline Derivatives. A Case of Self-Reproduction of Chirality[1,2]", *Journal of the American Chemical Society*, vol. 105, No. 16, pp. 5390-5398 (1983).

Urdiales, Jose L. et al., "Antiproliferative effect of dehydrodidemnin B (DDB), a depsipeptide isolated from Mediterranean tunicates", *Cancer Letters*, vol. 102, Nos. 1,2, pp. 31-37 (1996).

Vervoort, Helene et al., "Tamandarins A and B: New Cytotoxic Depsipeptides from a Brazilian Ascidian of the Family Didemnidae", *The Journal of Organic Chemistry*, vol. 65, No. 3, pp. 782-792 (2000).

De Vita, Jr., Vincent T, Samuel Hellman, and Steven A Rosenberg, eds. *Cancer: Principles and Practice of Oncology*, "Section 3 - Cancer of the Pancreas", Lippincott Williams & Wilkins, 7th Ed., 7 pages, (2005).

Tempero, Margaret, et al., *Clinical Practice Guidelines in Oncology* - v.2.2006 - "Pancreatic Adenocarcinoma" National Comprehensive Cancer Network, http://www.neen.org/professionals/physician_gls/PDF/pancreatic.pdf, 41 pages, (2006).

U.S. National Cancer Institute, U.S. National Institutes of Health, www.cancer.gov, "FactSheet", 6 pages, http://www.cancer.gov/cancertopics/factsheet/information/clinical-trials.

U.S. National Cancer Institute, U.S. National Institutes of Health, www.cancer.gov., "Pancreatic Cancer (PDQ®): Treatment", 3 pages, http://www.cancer.gov/cancertopics/pdq/treatment/pancreatic/healthprofessional.

\* cited by examiner

TREATMENT OF CANCERS

The present invention relates to the treatment of cancers using aplidine or related compounds which are aplidine analogs.

BACKGROUND OF INVENTION

Cancer comprises a group of malignant neoplasms that can be divided into two categories, carcinoma, comprising a majority of the cases observed in the clinics, and other less frequent cancers, which include leukaemia, lymphoma, central nervous system tumours and sarcoma. Carcinomas have their origin in epithelial tissues while sarcomas develop from connective tissues and those structures that had their origin in mesoderm tissues. Sarcomas can affect, for instance, muscle or bone and occur in the bones, bladder, kidneys, liver, lung, parotid or spleen.

Cancer is invasive and tends to metastasise to new sites. It spreads directly into surrounding tissues and also may be disseminated through the lymphatic and circulatory systems. Many treatments are available for cancer, including surgery and radiation for localised disease, and drugs. However, the efficacy of available treatments on many cancer types is limited, and new, improved forms of treatment showing clinical benefit are needed. This is especially true for those patients presenting with advanced and/or metastatic disease. It is also true for patients relapsing with progressive disease after having been previously treated with established therapies for which further treatment with the same therapy is mostly ineffective due to acquisition of resistance or to limitations in administration of the therapies due to associated toxicities.

Chemotherapy plays a significant part in cancer treatment, as it is required for treatment of advanced cancers with distant metastasis and often helpful for tumour reduction before surgery, and many anticancer drugs have been developed based on various modes of action.

Dehydrodidemnin B, now known as aplidine, is the subject of WO91/04985. It is related to compounds known as didemnins, and has the following structure:

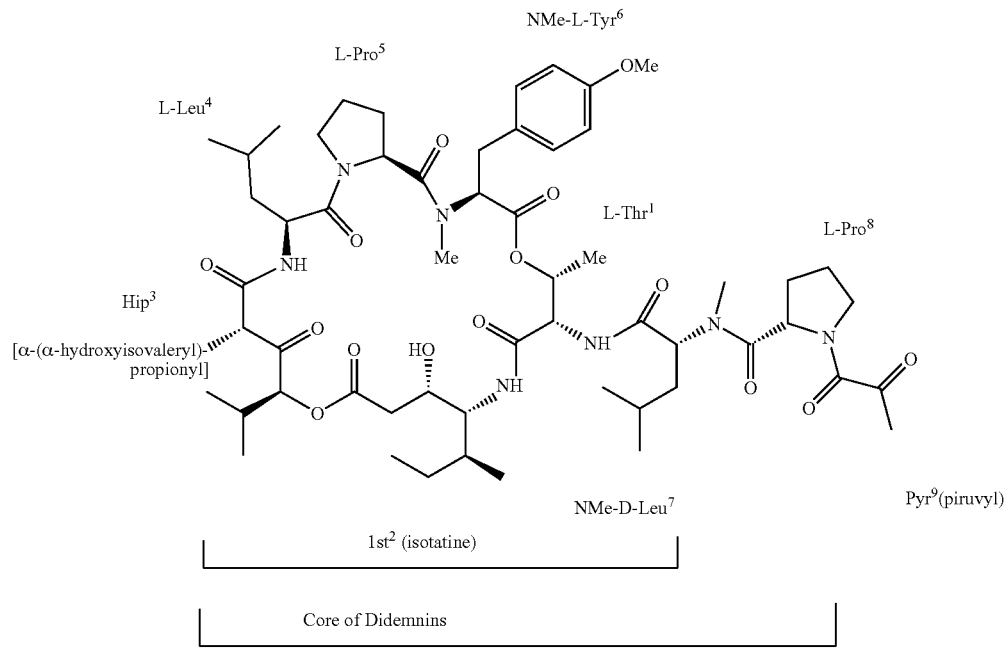

Aplidine

Further information on aplidine is to be found in, for example:

Jimeno, J., "Exploitation of marine microorganisms and invertebrates: Anticancer drugs from marine origin", IBC Conf Discov Drugs from Nat Novel Approaches New Sources (Dec 8-9, London) 1994, 1994

Faircloth, G. et al., "Dehydrodidemnin B (DDM) a new marine derived anticancer agent (MDA) with activity against experimental tumour models", 9th NCI-EORTC Symp New Drugs Cancer Ther (March 12-15, Amsterdam) 1996, Abst 111

Sakai, R. et al., "Structure-activity relationships of the didemnins", Journal of Medicinal Chemistry 1996, 39 (14): 2819

Urdiales, J. L. et al., "Antiproliferative effect of dehydrodidemnin B (DDB), a depsipeptide isolated from Mediterranean tunicates", Cancer Letters 1996, 102(1-2): 31

Faircloth, G. et al., "Preclinical characterization of aplidine (APD), a new marine anticancer depsipeptide (MADEP)", Proc Amer Assoc Cancer Res 1997, 38: Abst 692

Depenbrock, H. et al., "In vitro activity of aplidine, a new marine-derived anti-cancer compound, on freshly explanted clonogenic human tumour cells and haematopoietic precursor cells", British Journal of Cancer 1998, 78(6): 739

Faircloth, G. et al., "Aplidine (aplidine) is a novel marine-derived depsipeptide with in vivo antitumour activity", Proc Amer Assoc Cancer Res 1998, 39: Abst 1551

Faircloth, G. et al., "Preclinical development of aplidine, a novel marine-derived agent with potent antitumour activity", 10th NCI-EORTC Symp New Drugs Cancer Ther (June 16-19, Amsterdam) 1998, Abst 129

Mastbergen, S. C. et al., "Cytotoxicity and neurocytotoxicity of aplidine, a new marine anticancer agent evaluated using in vitro assays", 10th NCI-EORTC Symp New Drugs Cancer Ther (June 16-19, Amsterdam) 1998, Abst 131

In preclinical studies, aplidine had dose-dependent cytotoxic activity against the two epithelial-like cell lines, CT-1 and CT-2, and the human colon cancer cell line, HT-29. The most proliferative line, CT-2, was the most sensitive to aplidine. In addition the compound decreased ornithine decarboxylase activity in all three cell lines (Lobo C, Garcia-Pozo S G, et al. Effect of dehydrodidemnin B on human colon carcinoma cell lines. Anticancer Research. 17: 333-336, Jan-Feb 1997). In a similar study, aplidine 50 mmol/L inhibited the growth of the breast cancer cell lines, MDA-MB231 and MCF-7 by 17 and 47%, respectively. A significant increase in spermidine and spermine was observed in the treated cells (Gomezfabre P M, Depedro E, et al. Polyamine contents of human breast cancer cells treated with the cytotoxic agents chlorpheniramine and dehydrodidemnin B. Cancer Letters. 113: 141-144, 26 Feb 1997). Flow cytometric analysis showed that aplidine did not induce any apparent cell cycle pertubations (Erba E, Balconi G, et al. Cell cycle phases pertubations induced by new natural marine compounds. Annals of Oncology. 7 (Suppl. 1): 82, 1996). In mice, aplidine was active against implanted P388 leukaemia and B16 melanoma, with an optimal dose of 160 micro/kg. Unlike didemnin B, aplidine was active in SC implanted lewis lung carcinomas (Faircloth G, Rinehart K, et al. Dehydrodidemnin B a new marine derived anticancer agent with activity against experimental tumour models. Annals of Oncology. 7 (Suppl. 1): 34, 1996).

Continuous exposure to low concentrations of aplidine inhibited the growth of a number of tumour cell lines, including non-Hodgkin's lymphoma, melanoma and breast, melanoma, ovarian and non-small cell lung cancers. The magnitude of effect was dependent on the time of exposure and appeared to be achievable at non-myelotoxic concentrations. Non-small cell lung cancer, breast cancer and melanoma cell lines were sensitive to a continuous exposure to aplidine at concentrations of >=0.001 micromol/L. Aplidine had similar toxicity to doxorubicin against clonogenic haematopoietic stem cells (Depenbrock H, Peter R, et al. In vitro activity of aplidine, a new marine-derived anti-cancer compound, on freshly explanted clonogenic human tumour cells and haematopoietic precursor cells. British Journal of Cancer. 78: 739-744, No. 6, September 1998).

Aplidine had significant activity against mice bearing human cancer xenografts. At a maximum tolerated dose of 2.1 mg/kg, aplidine produced near complete remissions in some animals with a treated/control (T/C) tumour ratio of 9%. At 1.25 mg/kg, significant activity was seen against gastric tumours (T/C 14%) and prostate tumour growth inhibition was also observed (T/C 25%) (Faircloth G, Grant W, et al. Preclinical development of aplidine, a novel marine-derived agent with potent antitumour activity. Annals of Oncology. 9 (Suppl. 2): 34, 1998).

Aplidine is related to other compounds of potential use against cancer, notably the didemnins. Aplidine is itself a dehydrodidemnin.

Examples of the related didmenins and other such compounds, which we generally refer to as aplidine analogues, are to be found in:

a) Rinehart K L, Kishore V, Bible K C, Sakai R, Sullins D W, Li K M. Didemnins and tunichlorin: novel natural products from the marine tunicate Trididemnum solidum.
   J Nat Prod. 1988 January-February; 51(1):1-21.
   Erratum in:
   J Nat Prod 1988 May-June; 51(3):624 b) Rinehart K L Jr, Gloer J B, Wilson G R, Hughes R G Jr, Li L H, Renis H E, McGovren J P.
   Antiviral and antitumor compounds from tunicates.
   Fed Proc. 1983 January; 42(1):87-90.

c) Rinehart K L Jr, Gloer J B, Hughes R G Jr, Renis H E, McGovren J P, Swynenberg E B, Stringfellow D A, Kuentzel S L, Li L H.
   Didemnins: antiviral and antitumor depsipeptides from a caribbean tunicate.
   Science. May 22, 1981; 212(4497):933-5.

d) Vervoort H, Fenical W, Epifanio R A.
   Tamandarins A and B: new cytotoxic depsipeptides from a Brazilian ascidian of the family Didemnidae.
   J Org Chem. Feb. 11, 2000; 65(3):782-92.

e) PCT/GB01/02901.
   Synthetic methods for aplidine and new antitumoral derivatives Filing Date 2 Jul. 2001

The article (d) relates to aplidine analogues called tamandarines, notably tamandarine A and tamandarine B:

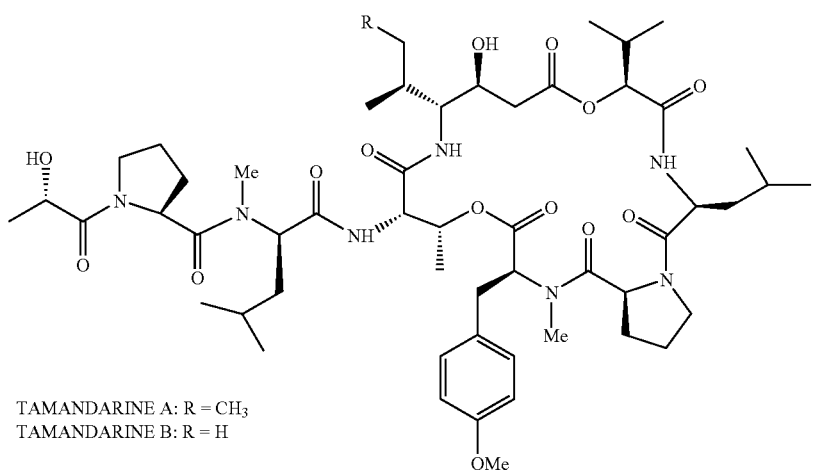

TAMANDARINE A: R = CH₃
TAMANDARINE B: R = H

SUMMARY OF INVENTION

We have developed improved methods to treat human patients with aplidine compounds, using muscle protectors such as L-carnitine. The aplidine compounds comprise aplidine itself, and aplidine analogues.

Embodiments of the Invention

The present invention provides a method of treating any mammal, notably a human, affected by cancer which comprises administering to the affected individual a therapeutically effective amount of an aplidine compound, being aplidine or an aplidine analogue, or a pharmaceutical composition thereof, and a skeletal muscle protector.

The aplidine compound and muscle protector are usually administered as separate compositions with different dosing regimes.

The invention further provides a method of reducing the side effects of an aplidine compound, which involves administering a muscle protector such as L-carnitine. A method is also provided for enhancing the Recommended Dose of an aplidine compound, which involves administering a muscle protector.

The present invention also relates to combination pharmaceutical preparations, which separately or together contain an aplidine compound and a skeletal muscle protector, as well as processes for their preparation. The combination preparations are for simultaneous or sequential use.

More particularly, the invention provides: the use of an aplidine compound in the preparation of a medicament for the treatment of a cancer by administering aplidine or an aplidine analog and a skeletal muscle preotector; the use of a skeletal muscle protector in the preparation of a medicament for the treatment of a cancer by administering aplidine or an aplidine analogue and a skeletal muscle preotector; and the use of an aplidine compound and a skeletal muscle protector in the preparation of a medicament for the treatment of a cancer by administering aplidine or an aplidine analogue and a skeletal muscle preotector.

Examples of pharmaceutical compositions or medicaments include liquids (solutions, suspensions or emulsions) with suitable composition for intravenous administration, and they may contain the pure compound or in combination with any carrier or other pharmacologically active compounds.

Administration of an aplidine compound or the aplidine compositions of the present invention is based on a Dosing Protocol preferably by intravenous infusion. We prefer that infusion times of up to 72 hours are used, more preferably 1 to 24 hours, with about 1, about 3 or about 24 hours most preferred. Short infusion times which allow treatment to be carried out without an overnight stay in hospital are especially desirable. However, infusion may be around 24 hours or even longer if required. Infusion may be carried out at suitable intervals with varying patterns, illustratively once a week, twice a week, or more frequently per week, repeated each week optionally with gaps of typically one week.

Examples of dosing regimes with and without carnitine are given in the following table:

| Schedule | maximum tolerated dose, MTD | dose-limiting toxicity | recommended dose, RD |
|---|---|---|---|
| Aplidine weekly 24 hour infusion for 3 weeks, 1 week rest | 4500 | Muscular/hepatic | 3750 |
| Aplidine weekly 1 hour infusion for 3 weeks, 1 week rest | 3600 | Muscular | 3250 |
| Aplidine 24 hour infusion every 2 weeks | 6000 | Muscular | 5000 |
| Aplidine 24 hour infusion every 2 weeks, L-carnitine daily | 8000 | Flu-like syndrome | 7000 |
| Aplidine 1-hour infusion for 5 consecutive days every 3 weeks | 1500 × 5 | Muscular/long lasting emesis | 1350 × 5 |

The correct dosage of the compound will vary according to the particular formulation, the mode of application, and the particular situs, host and tumour being treated. Other factors like age, body weight, sex, diet, time of administration, rate of excretion, condition of the host, drug combinations, reaction sensitivities and severity of the disease shall be taken into account. Administration can be carried out continuously or periodically within the maximum tolerated dose.

The preferred aplidine compound is aplidine, though the invention can be employed for the administration of aplidine analogues including those described in the documents (a) to (e) mentioned in the introduction. These documents are specifically incorporated herein by reference. Examples of the aplidine analogues include didemnin A, didemnin B, didemnin C, didemnin D and didemnin E, as well as all the compounds prepared in the PCT/GB01/02901.

The preferred muscle protector is L-carnitine, though racemic carnitine, precursors and derivatives of L-carnitine can be employed. Examples of precursors and derivatives include acetylcarnitine and other esters of carnitine and fatty acids or other organic acids. Suitable dosages include 0.05 to 0.2 g/kg, more suitably 0.075 to 0.15 g/kg, preferably about 0.1 g/kg L-carnitine/day. These dosages can be varied as appropriate to suit other muscle protectors. It is convenient to administer the L-carnitine or other muscle protector in 3 divided portions, though other dosing regimes can be employed. In one currently preferred procedure, the dose of L-carnitine is not less than 3.5 g/day, such as 1.5 g three times a day.

As well as adminstering a muscle protector, the aplidine compound and compositions of this invention may be used with other drugs to provide a combination therapy. The other drugs may form part of the same composition as the aplidine, or be provided as a separate composition for administration at the same time or a different time. The identity of the other drug is not particularly limited, and suitable candidates include:

a) drugs with antimitotic effects, especially those which target cytoskeletal elements, including microtubule modulators such as taxane drugs (such as taxol, paclitaxel, taxotere, docetaxel), podophylotoxins or vinca alkaloids (vincristine, vinblastine);

b) antimetabolite drugs (such as 5-fluorouracil, cytarabine, gemcitabine, purine analogues such as pentostatin, methotrexate);

c) alkylating agents or nitrogen mustards (such as nitrosoureas, cyclophosphamide or ifosphamide);

d) drugs which target DNA such as the antracycline drugs adriamycin, doxorubicin, pharmorubicin or epirubicin;

e) drugs with target topoisomerases such as etoposide;

f) hormones and hormone agonists or antagonists such as estrogens, antiestrogens (tamoxifen and related compounds) and androgens, flutamide, leuprorelin, goserelin, cyprotrone or octreotide;
g) drugs which target signal transduction in tumour cells including antibody derivatives such as herceptin;
h) alkylating drugs such as platinum drugs (cis-platin, carbonplatin, oxaliplatin, paraplidineatin) or nitrosoureas;
i) drugs potentially affecting metastasis of tumours such as matrix metalloproteinase inhibitors;
j) gene therapy and antisense agents;
k) antibody therapeutics;
l) other bioactive compounds of marine origin, notably kahalalide F or the ecteinascidins such as et-743;
m) other drugs which combat side effects of aplidine such as antiemetics;
o) more generally drugs which allow aplidine to be dosed at the Recommended Dose and manage toxicity.

We have further found that aplidine inhibits expression of the gene (FLT1) encoding the receptor of the Vascular Endothelial Growth Factor (VEGF). In addition, aplidine has been found to severely inhibit production of the VEGF protein itself by tumour cells.

VEGF secretion by a cell mass, in particular a tumour cell mass, causes de novo vascularization (angiogenesis) leading to new blood vessels forming towards the cell mass and establishing a network of capillaries that is able to supply it with irrigation for its sustained proliferation. These effects, in particular the demonstrated abolition of production of VEGF by tumour cells are expected to severely inhibit the ability of the tumour cells to bring forth angiogenesis. In addition, VEGF is required directly by some hematopoietic tumour cells (such as MOLT4 human leukaemia cells) as a growth factor.

Thus aplidine can be predicted to have an inhibitory effect on de novo vascularization of growing primary tumours or metastases, therefore inhibiting growth of the tumours, which are known to require vascularization for growth. Aplidine should also be active on hematopoietic tumours.

Bladder tumours are one type of tumour over-expressing the receptor to Epithelial Growth Factor (EGF), which leads to upregulation of VEGF and the VEGF receptor. Binding of VEGF to its receptor is believed to lead to cell growth stimulation by means of transitory local calcium ion changes among other mechanisms for signalling. A compound inhibiting VEGF action is expected to be inhibitory to such tumours.

Experimentally, aplidine has been found to have exceedingly high activity on human bladder cancer (giving complete remissions in some animal models), in accordance with the prediction.

Aplidine can be predicted to have a broad spectrum antitumour activity due to its effects on a large number of tumours.

The effect of VEGF is more relevant because it involves an inhibition of new blood vessels. In addition to effects on blood vessels, certain tumours required VEGF directly for cell growth (i.e. leukaemia, lymphomas, bladder tumours and ovarian tumours).

Responses in cancer patients have been observed in clinical trials with aplidine, demonstrating usefulness of the method of treatment.

Phase I clinical studies and pharmacokinetic analysis demonstrate that aplidine presents a positive therapeutic window with manageable toxicity in the range of dosage required for clinical efficacy in the treatment of cancer patients. In particular, the present invention is expected to be of benefit for treatment of renal cancer, melanoma, medullary thyroid carcinoma, lung neuroendocrine tumors, non-Hodgkin lymphoma, colorectal cancer, non-small cell lung cancer, among others.

The method consists of administration of drug by intravenous infusion over a period of 72 hrs or less at the recommended dose level (RD) with or without combination with other therapeutic agents, in conjunction with the administration of a muscle protector.

Aplidine is supplied and stored as a sterile lyophilised product, consisting of aplidine and excipient in a formulation adequate for therapeutic use.

Solubilised aplidine shows substantial degradation under heat and light stress testing conditions, and a lyophilised dosage form was developed, see WO99/42125 incorporated herein by reference. In a currently preferred embodiment freeze-drying was performed from a 500 mg/mL solution of aplidine in 40% (v/v) tert-butanol in Water for Injection (Wfl) containing 25 mg/mL D-mannitol as bulking agent. The prototype, containing 500 mg aplidine and 25 mg D-mannitol as bulking agent per vial was found to be the optimal formulation in terms of solubility, length of lyophilisation cycle and dosage requirements in the clinical studies. The optimal reconstitution solution was found to be 15/15/70% (v/v/v) Cremaphor EL/ethanol/Wfl (CEW). Both reconstituted product and dilutions (up to 1:100 v/v) of the reconstituted product with normal saline appeared to be stable for at least 24 hours after preparation. Shelf-life data, available thus far, show that the formulation is stable for at least 1 year when stored at 4° C. in the dark.

Preparation of the infusion solution is also performed under aseptic conditions by withdrawing the reconstituted solution volume corresponding to dosage calculated for each patient, and slowly injecting the required reconstituted solution volume into an infusion bag or bottle containing between 100 and 1000 ml of 0.9% sodium chloride, after which the whole is homogenised by slow manual shaking.

The aplidine infusion solution should be administered intravenously, as soon as possible, within 48 hours after preparation. PVC and polyethylene infusion systems, as well as clear glass are preferred container and conduit materials.

The administration is performed in cycles, in the preferred application method, an intravenous infusion of aplidine is given to the patients the first week of each cycle, the patients are allowed to recover for the remainder of the cycle. The preferred duration of each cycle is of either 3 or 4 weeks; multiple cycles can be given as needed. The drug may also be administered each of the first days of each cycle. Dose delays and/or dose reductions and schedule adjustments are performed as needed depending on individual patient tolerance of treatments, in particular dose reductions are recommended for patients with higher than normal serum levels of liver transaminases or alkaline phosphatase, or bilrubin.

The Recommended Dose (RD) is the highest dose which can be safely administered to a patient producing tolerable, manageable and reversibly toxicity according to the Common Toxicity Criteria established by the National Cancer Institute, (USA) with no more than 2 out of 6 patients presenting any dose limiting toxicities (DLT). Guidelines for cancer therapy frequently call for administration of chemotherapeutic agents at the highest safe dose at which toxicity is manageable in order to achieve maximum efficacy (DeVita, V. T. Jr., Hellman, S. and Rosenberg, S. A., Cancer: Principles and Practice of Oncology, 3rd ed., 1989, Lipincott, Philadelphia).

DLTs for aplidine using this method of treatment were determined in clinical studies. These studies established a recommended dose level for differing kinds of dosing protocols.

Aplidine can be safely administered at a dosage level at or below the Recommended Dose (RD).

Infusion is currently the preferred procedure, with typical regimes including the following:
- 24 hour infusion weekly for a number of weeks, say three weeks, followed by one week rest;
- biweekly 24 hour infusion;
- 1 hour infusion weekly for 3 weeks every 4 weeks;
- daily infusion of say 1 hour×5 days q 3 weeks; and
- infusion of say 3 hours every other week.

In particular, reference is made to the Examples and related discussion in our copending WO 0135974.

Previously the principal biological responses reported to the administration of aplidine had been observed in animal or in vitro models, known to be notoriously inaccurate concerning their usefulness to predict responses in human patients, or in human patients in experimental settings where an effective, safe method of treatment was unavailable (either the dosage used was a toxic dose significantly elevated over the recommended dose or the administration schedule was not appropriate).

In clinical trials using the method of this invention, appropriate plasma levels were achieved in patients at RD, and most importantly, objectively measurable responses demonstrated evidence of clinical benefit to patients.

Definitions for patient toxicities are adopted from WHO Criteria and the responses determined following WHO Response Criteria.

Objective responses were obtained in patients with advanced and/or metastatic cancers refractory to previous treatments.

In particular treatment with this method has shown responses in cancer patients with advanced and/or metastatic disease, which exhibited progressive disease after having been previously treated with established therapies.

More generally, the invention involves the use of a muscle protector in conjunction with aplidine therapy. We have found in particular that carnitine is beneficial in treating myotoxicity that is associated with chemotherapy with the experimental drug aplidine. In Phase I trials when using a 24-hour infusion of aplidine, 4500 mcg/m$^2$ every week, then 6000 mcg/m$^2$ every second week, some subjects experienced some form of muscular and skeletal toxicity characterized by muscle cramping, pain and myopathic weakness. They also showed measurable increases in serum creatine kinase, an indicator of muscle breakdown and damage. When L-carnitine 4.5 g/day was added to the therapy (at doses of 1.5 g three times daily), or 0.1 mg/kg (at doses of 0.033 mg 3 times daily) patients were able to tolerate doses of aplidine up to 6000 mcg/m 2 every second week. The beneficial effect, as seen in normal creatine kinase values, lasted throughout the study period of at least 13 weeks. Therefore, muscle protectors such as L-carnitine is a useful myoprotector for patients being treated with aplidine or an aplidine analogue.

A preferred method of this invention therefore involves identifying cancer patients who have been treated for cancer, particularly patients who have received chemotherapy, and treating them with an aplidine compound, especially aplidine.

The present PCT application claims priority from earlier patent applications. We specifically incorporate them by reference, especialy where there is disclosure not carried forward to the present specification and where that disclosure night be relevant to the present invention.

EXAMPLES OF THE INVENTION

Example 1

Figure 1:
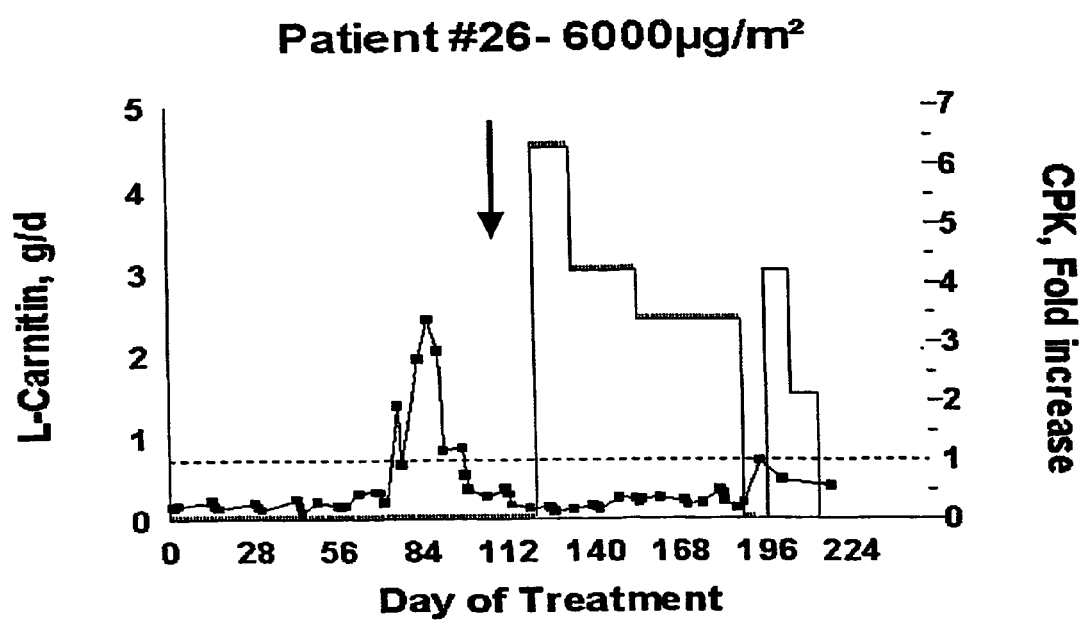
FIGS. 1 and 2 show the relationship of muscle enzyme changes for two patients in relationship to administration of aplidine and L-carnitine.

A phase I and pharmacokinetic study of aplidine, given as a 24 h continuous infusion every other week in patients with solid tumours and non-Hodgkin lymphoma

| Patient Characteristics | |
|---|---|
| Number of patients | 43 |
| Median age, years (ranges) | 52 (18-71) |
| ECOG performed status | |
| 0 | 19 |
| 1 | 21 |
| 2 | 2 |
| Prior radiotherapy | 27 |
| Prior chemotherapy (No. regimens) | |
| 1 | 7 |
| 2 | 5 |
| ≧3 | 29 |
| Tumour type | |
| Lung | 6 |
| Colorectal | 8 |
| Kidney | 5 |
| Breast | 4 |
| Pancreas | 4 |
| Lymphoma | 3 |
| Ovary | 2 |
| Thyroid | 3 |
| Bone | 1 |
| Melanoma | 1 |
| Prostate | 1 |
| Uterus | 1 |
| Mesothelioma | 1 |
| Gastric | 1 |
| Other | 2 |

| Patient Accrual and Dose Escalation | | | |
|---|---|---|---|
| Dose level | Dose (mcg/m$^2$/2 wks) | No. patients | No. Cycles (range) |
| I | 200 | 3 | 5 (1-3) |
| II | 400 | 3 | 6 (2-2) |
| III | 800 | 3 | 9 (2-4) |
| IV | 1600 | 6 | 11 (1-2) |
| V | 3200 | 3 | 5 (1-2) |
| VI | 4000 | 3 | 8 (2-4) |
| VII | 5000 | 3 | 6 (2-2) |
| VIII | 6000 | 12 | 26 (1-6+) |
| IX | 7000 | 7 | 12 (1-4+) |
| Total | | | |

*cycle definition: 2bi-weekly infusions

| | Worst Toxicities Per Patient | | | | | | | | |
|---|---|---|---|---|---|---|---|---|---|
| Dose level | 200 | 400 | 800 | 1600 | 3200 | 4000 | 5000 | 6000 | 7000 |
| No. patients | 3 | 3 | 3 | 6 | 3 | 3 | 3 | 12 | 7 |
| Nausea/vomiting G2 (G3) | 2 | 1 | — | 4 | (1) | 2 | 1 | 2 | 1 |
| Flushing G1 | — | — | 1 | — | 1 | 1 | — | — | 1 |
| Asthenia G2 (G3) | — | 2 | — | 2(1) | 1 | 1 | (1) | 6 | 2 |
| Muscle cramps G1 + G2 | — | — | 2 | 1 | 2 | 2 | 2 | 1 | — |
| Muscle pain G1 (G2) | — | — | — | — | (1) | 2 | 1 | 1(2) | 1 |
| Muscle weakness G1 (G2) | — | — | — | — | — | — | 1 | 1(1) | — |
| CPK elevation (G2 (G3) [G4] | — | — | — | — | — | — | (1) [1] | 1(1) | 1 |
| Transaminitis G2 (G3) | 1 | — | — | (1) | — | — | 1 | — | 1 |
| Hypertension G2 | — | 1 | — | — | — | — | — | — | — |
| Neutrophenia G4 | — | — | — | — | — | — | — | — | 1 |
| Pain central catheter G2 | — | — | — | — | — | 2 | — | — | — |

Characterisation of Muscular Toxicity (DLT)

Pat #27—Male patient with medullary thyroid carcinoma treated at 6000 μg/m² weekly had symptomatic G3 CPK with G2 muscular pain. Toxicity recovered within 3 weeks after treatment discontinuation.

3 patients (5000 and 6000 μg/m²) experienced a minor elevations of CPKs (≧G2), consisting of CPK MM (muscle) increase with no significant elevation of SPK MB (heart). A parallel elevation of the aldolase level was observed. Signs of improvement by using Carnitine supplements as skeletal muscle protectors are being reported. Muscle biopsies were performed in 2 patients; E/M: partial disappearance of thick filaments of myosin.

Pharmacokinetic Data

Aplidine appears to have a dose-linear PK profile (within the constraints imposed by the low sample size) Relatively high plasma CL: median (quartiles) value 252 (192-415 mL/min/m²) High interpatient CL variability (coefficient of variation of CL 62%) Intermediate to long t ½ with a median (quartiles) value of 23.8 (15.7-35.0 h)

Wide distribution, median (quartiles) Vss of 413 (274-638 L/m²) Preliminary compartmental analysis: plasma profiles are best fit by a first-order 2-compartment model with a rapid initial (median half-life 0.64 h) and a longer terminal phase (median half-life 25.8 h)

Aplidine Mytotoxicity Relationship with Pharmacokinetics

Muscular toxicity has appeared only at high doses and exposures after 24 h infusion Cmax values after 1 h infusion are already higher than those after 24 h infusion. Hence, a Cmax relationship may be ruled out The AUC values in the patients with myotoxicity are high but not the maximum It affected patients with high, sustained plasma concentrations of aplidine. The 3 patients with clear muscular toxicity had t ½ in excess of 44 h as compared to a median t ½ of 25.8 h after 24 h infusion Conclusions Drug induced muscular changes (expected to be the dose limiting toxicity), reported from dose level number III onwards (1800 mcg/m² to 5000 mcg/m²) is dose limiting toxicity at 6000 mcg/m² (1/9 pts) Antitumour activity has been also noted in patients with NHL and renal carcinoma The study is now investigating the feasibility of 6000-7000 mcg/m² every other week by using carnitine supplements as skeletal muscle protectors.

Example 2

Phase I studies of aplidine revealed aplidine myotoxicity.

Clinical Features

The presentation is variable among patients. Mild cases have muscle cramps (at doses from 3200 mcg/m2 every 2 weeks), while in more severe cases the symptoms are associated to reversible increases in creatin-kinase (CK) reaching up to grade 3. In the dose-limiting cases there is weakness of proximal distribution. The effect has a delayed onset, appearing after 3 to 8 (median 4) infusions of the drug.

Pathological Features

Light microscopy: just minimal necrosis or no changes at all (in most biopsied patients) or type II fiber atrophy (in a patient with gastric adenocarcinoma and concomitant long term 10 mg/d prednisone). Electron microscopy: aspecific accumulation of glycogen and autophagocytic vacuoles, being the most important change the disappearance of thick filaments.

Relationship to Exposure

The maximum concentrations (Cmax) observed after 1 h infusion, before even hints of myotoxicity were found, were higher than those after doses related to myotoxicity 24 h infusion ruling out a Cmax relationship. The area under the curve (AUC) values in patients with myotoxicity tend to be high but not uniformly and not the maximum. Patients with dose-limiting myotoxicity had the longest terminal half-lives with the exception of a patient who received just 2 aplidine infusions, i.e. a treatment too short to be evaluable for myotoxicity. Another patient with myotoxicity had a short half life. Probably the relatively high AUC in some patients with muscular toxicity reflected the long half life. Hence, aplidine myotoxicity appears related to prolonged exposure rather than high exposure or concentrations.

Muscle Enzymes Changes

Figure 2:
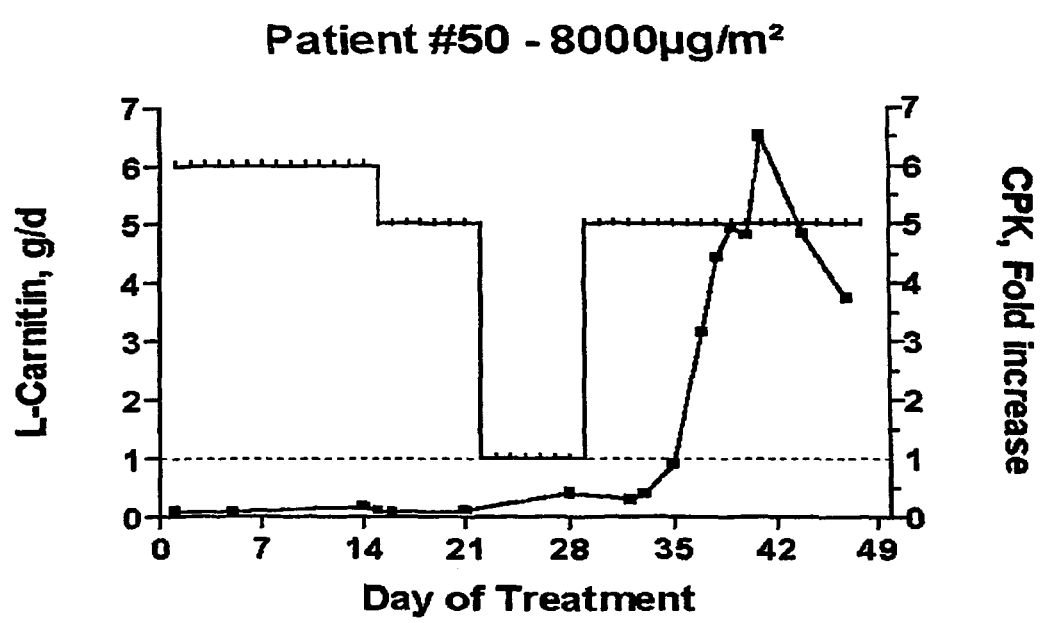

Examples of the relationship to aplidine and L-carnitine administration are shown in FIGS. 1 and 2. For both figures, aplidine was given every 14 days starting from Day 1. For FIG. 1, the arrow indicates omitted aplidine dose.

Corrective Measures

L-carnitine at a dose of 1.5 grams 3 times per day or 0.033 g/kg 3 times per day was started in all patients of study APL-A-003-98. In the study, 4 patients with prior skeletal muscle toxicity were able to continue treatment with no skeletal muscle symptoms and just transient grade 1 CK increases. Among the 11 patients receiving L-carnitine prophylaxis from the beginning in the above study there was just an asymptomatic G1 increase in CK. Two patients had symptomatic increases in CK (grade 3 associated to weakness & grade 1 associated to asthenia, respectively) after treatment at reduced doses (1 g for a week due to an administrative problem and irregular bad compliance respectively).

L-carnitine at the doses used in this study is well tolerated. The only toxicity reported to date is the presence of grade 1 abdominal discomfort and diarrhea. The dose may be decreased to manage the above effects. Initial graphical analysis of patients with increases in CK after decreased L-carnitine dose suggest that the dose should not be decreased below 3.5 grams per day.

In all ongoing studies a maximum tolerated dose (MTD) and a recommended dose (RD) without prophylactic L-carnitine (only allowed on a therapeutic basis) would be defined. Later in the study, systematic L-carnitine prophylaxis will be started and a new MTD and RD will be defined.

The possibility of tumor protection by L-carnitine was evaluated using a panel of 25 human tumor cell lines. Initial results are compatible with a lack of effect of L-carnitine on the antitumor activity of aplidine.

Figure 3:
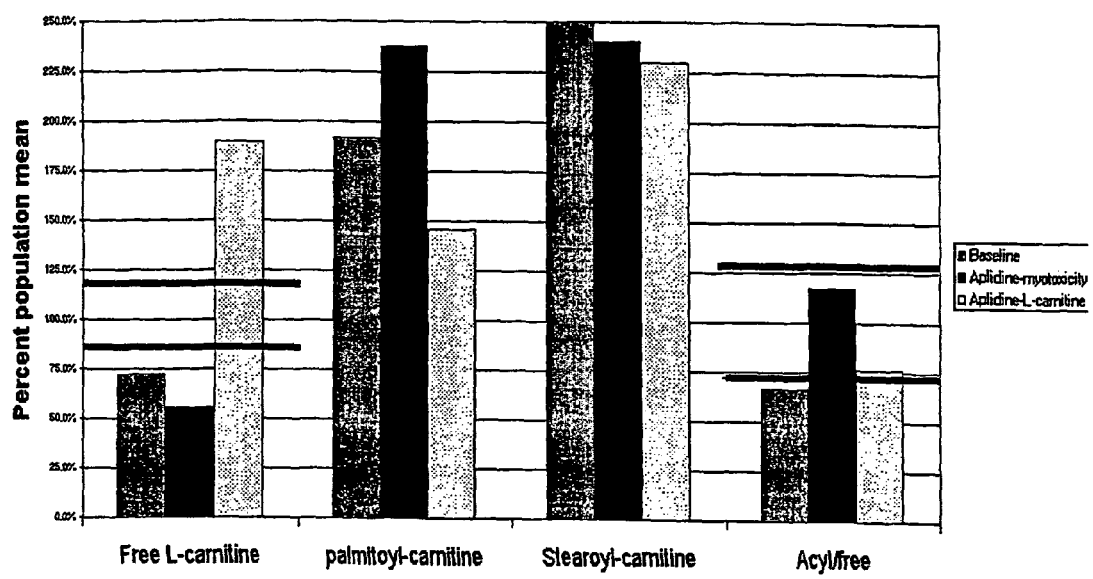
FIG. 3 shows the evolution of acylcarnitines for aplidine and aplidine-carnitine.

FIG. 3 shows the evolution of acylcarnitines, where the thick lines represent 95% CI for the normal population for the respective parameter.

Acylcarnitine Profile

It was measured by tandem mass spectrometry in plasma from a patient with clear toxicity (cramps+increased CK+weakness) at baseline, during toxicity and after aplidine treatment continued under L-carnitine protection. At baseline, there was decreased free L-carnitine, increased palmitoyl and steraroylcarnitine. During myotoxicity while on aplidine alone, free L-carnitine decreased while palmitoylcarnitine increased and stearoylcarnitine was stable L-Carnitine increased serum free carnitine up to supranormal values, while decreasing palmitoylcarnitine. Stearoylcarnitine was stable. Values for long chain acylcarnitines were less than half the diagnostic cutoff for CPT-II deficiency. Hence, this was not the underlying molecular defect (or at least not the only defect) present in this patient.

CONCLUSIONS

The dose-limiting factor for aplidine in 4 Phase I trials has been skeletal muscle toxicity. L-carnitine was assessed as a myoprotector for use in patients. The available clinical data demonstrates that L-carnitine prophylaxis enabled to increase aplidine MTD-RD by 33% and 40% respectively in the 24 h every other week infusion study, being the new dose-limiting factor non-muscular.

Phase II studies will be initiated using a RD of aplidine of 7 mg/m$^2$ and L-carnitine at an initial dose of 0.1 g/kg/day divided in 3 portions.

The invention claimed is:

1. A method of treating cancer in a patient which comprises administering aplidine in conjunction with L-carnitine, wherein the L-carnitine is administered in an amount effective for treating myotoxicity associated with chemotherapy with the aplidine compound.

2. A method according to claim 1, where the aplidine and L-carnitine are administered as separate compositions with different dosing regimes.

3. A method according to claim 1, wherein the L-carnitine is administered daily as divided doses.

4. The method according to claim 1, wherein the patient has already received treatment for cancer but was found to have a tumor refractory to the treatment.

5. The method of claim 1, wherein the aplidine is administered over a time period from 12 hours to 24 hours at intervals of from 2 to 4 weeks.

6. The method of claim 1, wherein the amount of L-carnitine that is administered is not less than 3.5 grams/day.

7. The method of claim 6, wherein the amount of L-carnitine that is administered is 4.5 grams/day.

8. The method of claim 7, wherein 1.5 grams of L-carnitine is administered three times a day.

9. A method for reducing the myotoxicity associated with chemotherapy with aplidine compounds, the method comprising aplidine, the method comprising administering aplidine to a patient in conjunction with L-carnitine, wherein the amount of the L-carnitine is sufficient to reduce the myotoxicity.

* * * * *

UNITED STATES PATENT AND TRADEMARK OFFICE
CERTIFICATE OF CORRECTION

PATENT NO. : 7,507,766 B2  Page 1 of 1
APPLICATION NO. : 10/398835
DATED : March 24, 2009
INVENTOR(S) : Lazaro et al.

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by 345 days Delete the phrase "by 345" and insert -- by 257 days --

Signed and Sealed this

Twenty-second Day of September, 2009

David J. Kappos
*Director of the United States Patent and Trademark Office*